United States Patent [19]
Watterson, III et al.

[11] Patent Number: 5,919,554
[45] Date of Patent: Jul. 6, 1999

[54] ANTIMICROBIAL FIBERGLASS REINFORCED PLASTIC COMPOSITE

[75] Inventors: Robert S. Watterson, III; William D. Hanrahan, both of Charlotte, N.C.

[73] Assignee: Microban Products Company, Huntersville, N.C.

[21] Appl. No.: 09/016,070

[22] Filed: Jan. 30, 1998

[51] Int. Cl.$^6$ .............................. B32B 9/00; B32B 27/00
[52] U.S. Cl. .............................. 428/201; 428/68; 428/76; 428/192; 428/206; 428/372; 428/378; 428/380; 428/394
[58] Field of Search ..................... 428/206, 372, 428/378, 380, 68, 76, 394, 192, 201; 264/46.4, 46.6

[56] References Cited

U.S. PATENT DOCUMENTS 5,670,255  9/1997  Temple et al. .......................... 428/392

Primary Examiner—Richard Weisberger
Attorney, Agent, or Firm—Dougherty & Associates

[57] ABSTRACT

A fiber reinforced plastic (FRP) composite having antimicrobial characteristics that inhibit bacterial growth includes a polyester resin composition and an antimicrobial agent incorporated therein. The polyester resin composition includes a polyester resin, high modulus fiber reinforcements, a curing catalyst and a polyester resin gelcoat. The antimicrobial agent is incorporated into the amorphous zones of the molecular structure of the polyester resin composition. A method for forming the FRP composite having antimicrobial characteristics that inhibit bacterial growth is also disclosed. The antimicrobial additive is incorporated into the amorphous zones of the molecular structure of the polyester resin composition using a solubilizing agent carrier system, thereby incorporating the antimicrobial agent into the FRP composite. The antimicrobial additive in the FRP composite, incorporated in the manner above, results in substantive controlled migration from the polyester resin to the surface of the FRP composite, until a point of equilibrium is reached.

22 Claims, 1 Drawing Sheet

ANTIMICROBIAL FIBERGLASS REINFORCED PLASTIC COMPOSITE

FIELD OF THE INVENTION

This invention relates generally to antimicrobial fiber reinforced plastic (FRP) composites, and more particularly to FRP composites having antimicrobial compounds or chemicals embedded in a polyester resin containing composite.

BACKGROUND OF THE INVENTION

Fiber reinforced plastic (FRP) is widely used in numerous consumer products to provide a sturdy plastic structure having a desirable surface appearance. For example, FRP is incorporated into bath tubs, sinks and wash basins which are used in homes, hotels, hospitals, restaurants and other residential or commercial environments where such products are continuously exposed to water and a variety of chemicals. In another example, FRP is incorporated into the panels used in automobiles and recreation vehicles as well as into the hulls, decks and interiors of marine vessels, such as commercial and recreational fishing boats. FRP may be made with polyester resin to provide a composite material having tensile strength, impact strength, heat resistance, chemical resistance and a high quality surface finish which are desirable physical and mechanical characteristics for FRP based products used in the previously described environments.

However, the surface of these FRP based products are under constant exposure to bacteria, fungi and microbes that exist in their respective environments. For example, FRP based products, such as tubs and sinks, are used in bathrooms, kitchens, hospitals and other environments that are particularly associated with pathogen development and proliferation. The presence of humidity or moisture in these environments, or any environment, is conducive to growth of pathogens. Additionally, FRP based products used in the marine market, such as boats, are exposed to salt water and fresh water environments which are havens for algae, as well as aquatic thriving pathogens, and which are also conducive to algal, fungal and bacterial growth. These bacteria, fungi and other pathogens can grow and multiply on the surfaces of the FRP based products, and significant levels of microbial contamination can build over time.

One proposed method to counter the presence and growth of microbes on the surface of FRP based products is to apply a disinfectant to the surface, such as by spraying or wiping the surface. Unfortunately, the applied disinfectant provides only temporary removal of the microbes on the surface, but, as previously mentioned, the associated environment is a continuous resource for further contamination. Reapplication of the disinfectant is costly, time consuming, non-durable and only temporarily counters the presence and growth of microbes. Additionally, by applying the disinfectant or other biocide to the surface of the FRP based product, a residual of the disinfectant or biocide enters the environment and may negatively impact the environment, especially in an aquatic environment.

What is needed is an antimicrobial agent that can be incorporated into an FRP composite at the time of manufacture, that is free from toxic effect and is durable over the lifespan of the FRP composite and which will migrate to the surface as needed to provide appropriate protection. However, by incorporating an additional material into the FRP composite, one would expect a diminishment of the physical and mechanical properties of the FRP based product because a corresponding amount of an FRP constituent, e.g., fiber or polymer resin, would be replaced by the additional material. Further needed is an FRP composite having antimicrobial compounds or chemicals embedded in the composite that has physical and mechanical characteristics similar to FRP composites that do not have antimicrobial compound or chemicals embedded in the composite.

SUMMARY OF THE INVENTION

The present invention is an FRP composite having antimicrobial characteristics that inhibits bacterial, fungal, microbial and other pathogen growth and method for producing the FRP composite. The antimicrobial agents, compounds or chemicals are embedded in the FRP composite during manufacture. Further, the present invention is an FRP composite having antimicrobial compounds or chemicals embedded in the composite that has physical and mechanical characteristics similar to FRP composites that do not have antimicrobial compound or chemicals embedded in the composite.

Using a solubilizing agent carrier system, an antimicrobial additive is incorporated into the amorphous zones of the molecular structure of a polyester resin from which FRP composites are formed, thereby incorporating the antimicrobial agent into the FRP composite. The levels of antimicrobial additive in the FRP composite, incorporated in the manner above, results in substantive controlled migration from the amorphous zones of the molecular structure of the polyester resin to the surface of the FRP composite, until a point of equilibrium is reached. As the surface of the FRP composite is abraded during use and this equilibrium is disrupted, additional migration is stimulated, until equilibrium is again reached. Products formed with the FRP composite include, without limitation, bathtubs, sinks, wash basins, automotive panels, architectural panels, boats, fitness products, swimming pools, etc.

The FRP composite is formed by selecting the antimicrobial agent and the solubilizing agent carrier system to correspond to the polyester resin, combining the solubilizing agent carrier system with the selected antimicrobial agent, incorporating the antimicrobial agent into the polyester resin, depositing the polyester resin composition and glass fibers or other high modulus fibers on a desired mold or product-forming surface and curing the polyester resin that can include the deposited high modulus fibers.

OBJECTS OF THE INVENTION

The principal object of the invention is to provide an FRP composite having antimicrobial protection incorporated in the polymeric material of the FRP composite.

Another, more particular object of the invention is to provide an FRP composite having antimicrobial protection for a product formed with the FRP composite in a cost-effective, non-toxic and durable way.

Another object of the invention is to provide an FRP composite having antimicrobial compounds or chemicals embedded in the composite that has physical, mechanical and surface appearance characteristics similar to FRP composites that do not have antimicrobial compound or chemicals embedded in the composite.

Another, more particular, object of the invention is to provide an FRP composite having antimicrobial compounds or chemicals embedded in the composite that has a chemical resistance, tensile strength, impact resistance and water absorption resistance similar to FRP composites that do not have antimicrobial compound chemicals embedded in the composite.

Another object of the invention is to provide an FRP composite having antimicrobial compounds or chemicals embedded in the composite that has a color fastness similar to FRP composites that do not have antimicrobial compound or chemicals embedded in the composite.

Another object of the invention is to provide antimicrobial protection that allows for controlled migration of an antimicrobial agent throughout a polyester polymer.

Another object of the invention is to provide a product formed from an FRP composite having an antimicrobial agent which is insoluble in water, thereby preventing any leaching of the agent during use of the product.

Another object of the invention is to provide an FRP composite in which an antimicrobial agent can migrate on demand from within the composite to the surface of the composite if some of the agent is removed from the surface by abrasion.

BRIEF DESCRIPTION OF THE DRAWINGS

These and other objects will become more fully understood by reference to the following detailed description of the invention and the appended drawing in which.

DETAILED DESCRIPTION OF THE INVENTION

Figure 1:
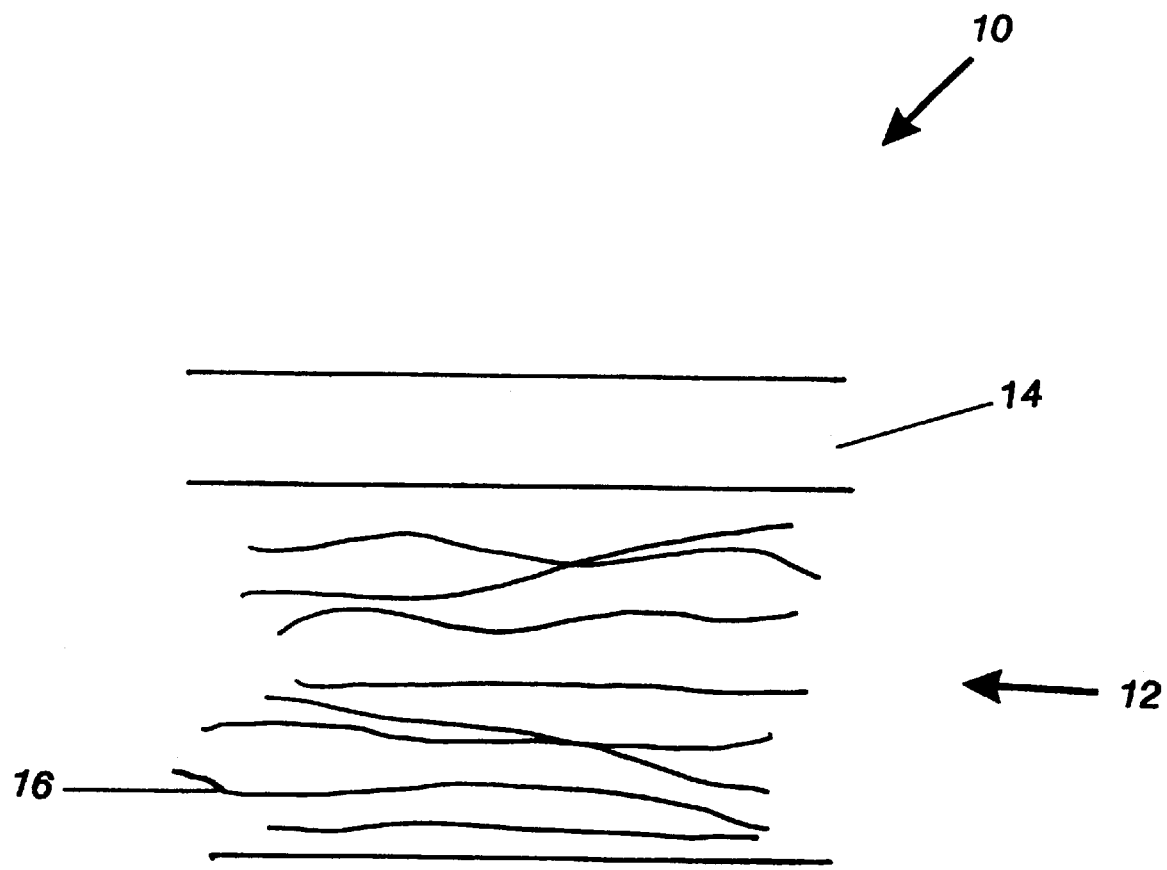
FIG. 1 is a cross-sectional view of a portion of a fiber reinforced plastic composite according to the present invention.

Polyester resins have a highly crystalline structure and exhibit "glassy" characteristics which make polyester resins very difficult for an antimicrobial agent embedded in the polyester resin to migrate within the polyester resin or to migrate from within the polyester resin to the surface of the polyester resin.

In the most basic form of the present invention, an FRP composite is made from a polyester resin composition and a broad spectrum antimicrobial agent that are batch processed and formed into a product. The polyester resin composition includes a polyester resin, fiber reinforcements and a curing catalyst. A polymer resin gelcoat, preferably a polyester resin gelcoat, may be optionally formed with the polyester resin composition to enhance the surface properties of the FRP composite. The broad spectrum antimicrobial agent associated therewith inhibits bacterial, fungal, viral and other pathogen growth. Preferably, an antimicrobial agent is associated or incorporated into the polyester resin from which the FRP composite is made. Thus, an effective amount of an antimicrobial substance (e.g., 5-chloro-2-(2, 4-dichlorophenoxy) phenol) is incorporated therein. Levels of active ingredients or antimicrobial substance range from 0.1% to 5% by weight of the FRP composite. The antimicrobial agent incorporated into the FRP composite surprisingly exhibits controlled migration through the polyester resin composition and polyester resin gelcoat despite the highly crystalline structure of the polyester resin.

Referring now to FIG. 1, in accordance with the present invention the FRP composite 10 includes a polyester resin composition, shown generally at 12, with an antimicrobial agent (not shown) integrally associated therein. Fiber reinforcements 16, preferably glass fibers, are incorporated in the polyester resin composition to provide structural and physical reinforcement to the polyester resin. A polyester resin gelcoat 14 adjacent the polyester resin composition 12 having fiber reinforcements 16 provides colorability, weatherability and a high quality surface appearance to the FRP composite.

The polyester resin is selected from conventional polyesters, modified or unmodified, used in the manufacture of FRP composites and is preferably an unsaturated polyester resin that may be processed at ambient temperatures. The fiber reinforcements 16 are selected from high modulus fibers such as glass fibers, carbon fibers, metal fibers and aromatic polyamide fibers but, as previously mentioned, are preferably glass fibers. The glass fibers may be chopped fibers ranging from about 5 mm to about 50 mm in length or may be continuous fibers in woven or non-woven forms. The curing catalyst is selected from benzoylperoxide, methethylketoneperoxide (MEKP), cumene hydroperoxide, t-butylperbenzoate and other conventional curing catalysts used in polyester resin FRP manufacture but is preferably MEKP.

The gelcoat 14 preferably utilizes the same type of resin as incorporated in the polyester resin composition having fiber reinforcements 16 for simplicity in the manufacture of the FRP composite 10 in addition to providing the high quality surface appearance and colorability, as previously mentioned. Additionally, the gelcoat 14 provides the FRP composite 10 with desirable ultraviolet radiation protection and weatherability. The thickness of the gelcoat 14 may be varied according to the desired interaction of the gelcoat with the environment. For example, a relatively thick gelcoat may be provided for surfaces exposed to abrasive environments. In a preferred embodiment of the present invention, the polyester resin gelcoat 14 has the antimicrobial agent integrally associated therein and described in further detail hereinbelow. Further, the polyester resin composition 12 and the polyester resin gelcoat 14 are colorable using conventional FRP coloring techniques, for example, by adding $TiO_2$ to whiten the FRP composite 10.

Core materials, such as balsa, rigid foam, corrugated paper and polyvinylchloride (PVC), may be introduced to the polyester resin composition 12 during the manufacture of the FRP composite 10 to provide thickness or dimension while minimally contributing to the weight of the FRP composite. A filler, for example a mineral filler, may also be introduced to the polyester resin composition 12 to reinforce, improve shrinkage and lower the manufacturing cost of the FRP composite 10. The types of fillers that may be introduced to the composition 12 include $TiO_2$, talc, mica, calcium carbonate, silica, plastic fibers, wood flour, cellulosic fiber, rice hulls and nut shells.

The FRP composite 10 having the antimicrobial agent incorporated therein is further resistant to growth of fungus, yeast, virus, and gram positive and gram negative bacteria including *S. aureus, E. coli, K. pneumoniae*, and Salmonella. The antimicrobial substance, which is non-toxic and free of heavy metal, is a chlorinated phenol and is preferably 5-chloro-2-(2,4-dichloro-phenoxy)phenol). An alternative antimicrobial agent is polyhexamethylene biguanide hydrochloride (PHMB). Other chemical compounds having known antimicrobial characteristics may also be used in the present invention. In a preferred embodiment of the present invention, the antimicrobial agent, 5-chloro-2-(2,4-dichlorophenoxy) phenol, is batch processed with the polyester resin and embedded in the FRP composite 10.

The antimicrobial agent incorporated into the polyester resin composition 12 and polyester resin gelcoat 14 is characterized by the agent moving from areas of high concentrations of agent to low concentrations of agent. The antimicrobial agent chosen is substantially insoluble in water which minimizes or eliminates any leaching of the agent during use of the FRP composite 10. By controlling the amount of antimicrobial agent incorporated into the polyester resin, migration of antimicrobial agent from the polyester resin to the surface of the FRP composite 10 is accomplished and optimized while maintaining the physical and mechanical properties of the FRP composite. Surprisingly, the FRP composite 10 having the antimicrobial agent associated therein has no substantial diminishment in physical and mechanical properties such as chemical resistance, tensile strength, impact strength and water absorption resistance.

Incorporating an appropriate amount of antimicrobial agent into the polyester resin is important. High concentrations of antimicrobial agent incorporated into the polyester resin can result in a degradation of the physical properties of the FRP composite 10 as well as an increase in production costs due to the increased expense of added antimicrobial agent. Low concentrations of antimicrobial agent incorporated into the polyester resin minimize the migration of antimicrobial agent to the surface of the FRP composite 10. An appropriate concentration range of antimicrobial agent in the polyester resin is necessary to effectively provide nontoxic, antimicrobial protection to the FRP composite 10 without sacrificing desirable physical properties of the FRP composite and incurring unnecessary production costs.

The antimicrobial agent is incorporated into a polyester resin master batch prior to forming the FRP composite 10. The antimicrobial agent is combined in a pre-determined amount, corresponding to a desired efficacy of the FRP composite 10, with a solubilizing agent carrier system, for example a plasticizer, compatible with the antimicrobial agent and introduced to the polyester resin master batch. For example, 5-chloro-2-(2,4-dichlorophenoxy)phenol was combined with the solubilizing agent carrier system and incorporated into the amorphous zones of the polyester resin during manufacture of the FRP composite 10. The polyester resin master batch having the antimicrobial agent incorporated therein provides the polyester resin used in both the polyester resin composition 12 and the gelcoat 14.

Organic antimicrobial agents have limited incorporability into polymer compositions because organic antimicrobial agents typically have a vaporization point less than the temperatures involved during formation of the polymer compositions. For example, 5-chloro-2-(2,4-dichlorophenoxy)phenol has a range of liquid phase from about 135° F. to about 165° F. and a vaporization point of about 400° F., whereas the temperatures generally associated with forming plastics are typically above 400° F. In that respect, if the antimicrobial agent is introduced into the polymer during manufacture, the agent typically vaporizes and does not become incorporated into the polymer. Alternatively, the antimicrobial agent may cross-link with the polymer. Cross-linking of the antimicrobial agent with the polymer is undesirable because the physical properties of the polymer can be degraded. Furthermore, cross-linking prevents the migration of antimicrobial agent through the polymer.

In the manufacture of the FRP composite 10 described herein, the polyester resin may be prepared at ambient temperature to minimize or eliminate vaporization of the antimicrobial agent. Furthermore, as previously described hereinabove, the antimicrobial agent survives incorporation into the polyester resin and exhibits controlled migration through the polyester resin composition 12 and gelcoat 14 despite the highly crystalline structure of the polyester resin and the presence of fiber reinforcements, fillers, core materials and colorant.

In a preferred embodiment of the present invention, the antimicrobial agent is associated with the polyester resin by first incorporating the agent into the solubilizing agent carrier system, as previously described, prior to the addition to the polyester resin master batch. The solubilizing agent carrier system containing the antimicrobial agent is combined with the polyester resin in liquid form using conventional batch processing techniques. In that respect, the antimicrobial agent is added as a component to the polyester resin in a let-down ratio which results in a final concentration of active ingredient of from about 0.1 percent to about 5.0 percent by weight of the FRP composite 10 and preferably from about 0.5 percent to about 2.0 percent.

The FRP composite 10 is produced using various conventional techniques including but not limited to spray forming and wet-laid sheet forming. A desired mold or product-forming surface is prepared using conventional cleaning techniques and a mold-release agent is applied to the surface of the mold. The polyester resin is batch processed at room temperature to incorporate the antimicrobial agent and the curing catalyst. The polyester resin gelcoat 14 having the antimicrobial agent incorporated therein is deposited or sprayed onto the desired mold. Then, the polyester resin composition having fiber reinforcements is applied onto the gelcoat 14.

In one embodiment, chopped glass fibers are deposited while the polyester resin is sprayed onto the gelcoat 14 to produce a flocculant. In an alternative embodiment, continuous glass fibers, in woven or non-woven form, are laid onto the gelcoat while the polyester resin is sprayed onto the fibers and gelcoat. Additionally, the continuous glass fibers, in woven or non-woven form, may be laid onto the gelcoat in a uniform direction or may be layered in multiple directions depending on the desired structural characteristics of the product formed with the FRP composite. Low heat is then applied to the FRP composite, for example by a drying oven, to initiate and accelerate cross-linking and curing of the polyester resin composition. After the polyester resin composition is cured, the formed FRP product is released from the mold. Different types of products formed from the FRP composite include bathtubs, sinks, wash basins, automotive panels, architectural panels, boats, fitness products, swimming pools and other home amenities.

In use, the antimicrobial agent migrates through the polyester resin composition 12 and the gelcoat 14 to the exposed surface of the FRP composite 10 from the amorphous zones of the polymer until equilibrium of the internal vapor pressure is reached. If the antimicrobial substance on the surface of the FRP composite 10 is removed by friction, or other abrading means, the antimicrobial agent moves to the surface until the agent's internal vapor pressure is once again at equilibrium.

SUMMARY OF THE ACHIEVEMENTS OF THE OBJECTS OF THE INVENTION

It is readily apparent that we have invented an FRP composite having antimicrobial protection incorporated in the polymeric material of the FRP composite. The present invention provides an FRP composite having antimicrobial protection for a product formed with the FRP composite in a cost-effective, non-toxic and durable way. The present invention provides an FRP composite having antimicrobial compounds or chemicals embedded in the composite that has physical, mechanical and surface appearance characteristics similar to FRP composites that do not have antimicrobial compound or chemicals embedded in the composite. The present invention provides an FRP composite having antimicrobial compounds or chemicals embedded in the composite that has a chemical resistance, tensile strength, impact resistance and water absorption resistance similar to FRP composites that do not have antimicrobial compound chemicals embedded in the composite. The present invention provides an FRP composite having antimicrobial compounds or chemicals embedded in the composite that has a color fastness similar to FRP composites that do not have antimicrobial compound or chemicals embedded in the composite. The present invention provides antimicrobial protection that allows for controlled migration of an antimicrobial agent throughout a polyester polymer. The present invention provides a product formed from an FRP composite having an antimicrobial agent which is insoluble in water, thereby preventing any leaching of the agent during use of the product. The present invention provides an FRP composite in which an antimicrobial agent can migrate on demand from within the composite to the surface of the composite if some of the agent is removed from the surface by abrasion.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. A fiber reinforced plastic (FRP) composite having antimicrobial characteristics comprising:
    a polyester resin composition comprising
        a polyester resin;
        a polyester resin gelcoat;
        high modulus fibers; and
        a curing catalyst; and
    an antimicrobial agent incorporated into said polyester resin composition;
    wherein said antimicrobial agent exhibits controlled migration through said polyester resin composition and to the surface of the FRP composite.

2. An FRP composite according to claim 1 wherein said antimicrobial agent exhibits controlled migration through said polyester resin composition when an imbalance of vapor pressure of the antimicrobial agent demands equalization.

3. An FRP composite according to claim 1 wherein said antimicrobial agent is a chlorinated phenol.

4. An FRP composite according to claim 1 wherein said antimicrobial agent is selected from the group comprising 5-chloro-2-(2,4-dichlorophenoxy)phenol and polyhexamethylene biguanide hydrochloride.

5. An FRP composite according to claim 1 wherein said antimicrobial agent is present in the composite in an amount of from about 0.1 percent to about 5.0 percent by weight.

6. An FRP composite according to claim 1 wherein said curing catalyst is selected from the group consisting of benzoylperoxide, methethylketoneperoxide, cumene hydroperoxide and t-butylperbenzoate.

7. An FRP composite according to claim 1 wherein said curing catalyst is methethylketoneperoxide.

8. An FRP composite according to claim 1 further comprising a filler selected from the group consisting of $TiO_2$, talc, mica, calcium carbonate, silica, plastic fibers, wood flour, cellulosic fiber, rice hulls and nut shells.

9. An FRP composite according to claim 1 further comprising a solubilizing agent carrier system for incorporating said antimicrobial agent with said polyester resin composition.

10. An FRP composite according to claim 1 further comprising:
    a core material for adding thickness and dimension to the FRP composite while minimally contributing to the weight of the FRP composite;
    wherein said core material is selected from the group consisting of $TIO_2$, polyvinylchloride, corrugated paper and rigid. foam.

11. An FRP composite according to claim 1 wherein said high modulus fibers are selected from the group consisting of glass fibers, carbon fibers, metal fibers and aromatic polyamide fibers.

12. A method for forming FRP composites having a polyester resin composition, the polyester resin composition having a polyester resin, high modulus fibers, a curing catalyst and an antimicrobial agent incorporated therein, the method comprising the steps of:
    selecting the antimicrobial agent and a solubilizing agent carrier system compatible with the polyester resin composition;
    combining the solubilizing agent carrier system with the selected antimicrobial agent;
    incorporating the antimicrobial agent into the polyester resin composition;
    depositing the polyester resin and the high modulus fibers onto a mold; and
    curing the polyester resin having the high modulus fibers;
    wherein the antimicrobial agent is incorporated into the polymeric material comprising the FRP composite, and wherein the antimicrobial agent exhibits controlled migration through the polymeric material and to the surface of the FRP composite.

13. A method for forming FRP composites according to claim 12 further comprising the steps of:
    coating the mold with a mold release agent; and
    providing a polyester resin gelcoat having the antimicrobial agent incorporated therein to the mold prior to said step of depositing.

14. A method for forming FRP composites according to claim 13 wherein said step of curing comprises the step of:
    combining a curing catalyst with the polyester resin composition and the polyester resin gelcoat.

15. A method for forming FRP composites according to claim 12 wherein said step of curing comprises the step of:
    combining a curing catalyst with the polyester resin composition.

16. A method for forming FRP composites according to claim 12 wherein said step of incorporating is performed at ambient temperatures.

17. A formed FRP composite having antimicrobial characteristics comprising:
    a polyester resin composition comprising
        a polyester resin;
        a polyester resin gelcoat;
        high modulus fibers; and
        a curing catalyst; and
    an antimicrobial agent incorporated with said polyester resin composition;
    wherein said antimicrobial agent exhibits controlled migration through said polyester resin composition and to the surface of the FRP composite.

18. A formed FRP composite according to claim 17 wherein said antimicrobial agent is present in the composite in an amount of from about 0.5 percent to about 2.0 percent by weight.

19. A formed FRP composite according to claim 17 wherein said antimicrobial agent exhibits controlled migration through said polyester resin composition when an imbalance of vapor pressure of the antimicrobial agent demands equalization.

20. A formed FRP composite according to claim 17 wherein said antimicrobial agent is a chlorinated phenol.

21. A formed FRP composite according to claim 17 wherein said antimicrobial agent is selected from the group comprising 5-chloro-2-(2,4-dichlorophenoxy)phenol and polyhexamethylene biguanide hydrochloride.

22. A formed FRP composite according to claim 17 wherein said high modulus fibers are selected from the group consisting of glass fibers, carbon fibers, metal fibers and aromatic polyamide fibers.

* * * * *